Figure 1:
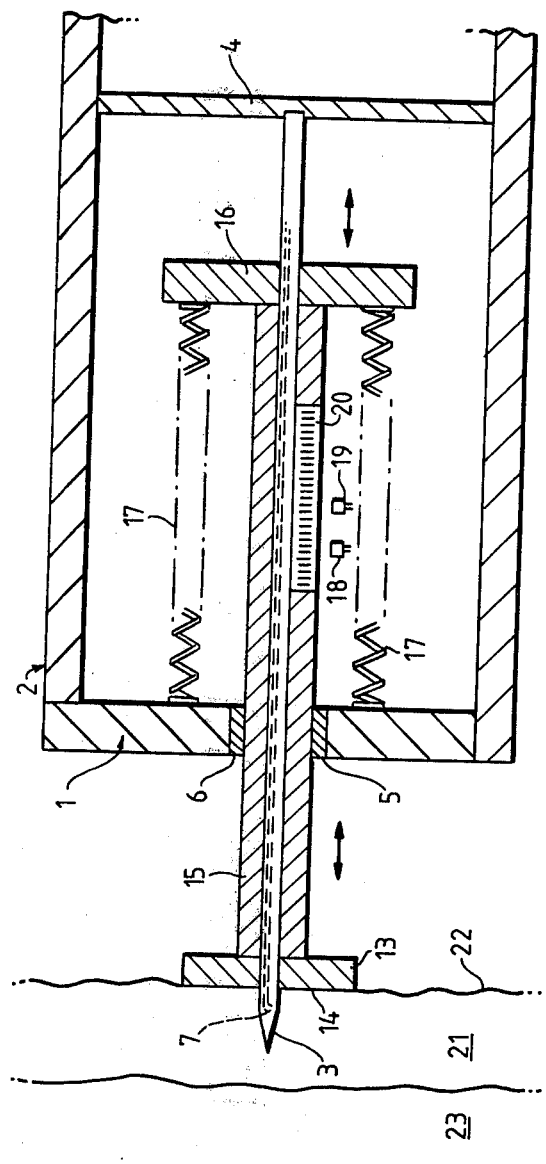

United States Patent [19]

Hennessy

[11] 4,270,274
[45] Jun. 2, 1981

[54] ANIMAL FAT INDICATOR

[76] Inventor: John B. Hennessy, Ahuroa, North Auckland, New Zealand

[21] Appl. No.: 122,069

[22] Filed: Feb. 15, 1980

[30] Foreign Application Priority Data

Feb. 16, 1979 [NZ] New Zealand .................. 189675

[51] Int. Cl.³ .................. G01B 5/02; G01B 11/06
[52] U.S. Cl. .................. 33/169 B; 116/306; 356/381
[58] Field of Search .................. 33/169 B, 125 C; 356/381

[56] References Cited

U.S. PATENT DOCUMENTS

| 1,894,025 | 1/1933 | Dennison et al. | 33/169 B X |
| 3,478,435 | 11/1969 | Cook | 33/169 B |
| 3,816,002 | 6/1974 | Wieg | 33/125 C X |
| 4,037,325 | 7/1977 | Weber et al. | 33/125 C |
| 4,078,313 | 3/1978 | Hennessy | 33/169 B |

Primary Examiner—Daniel M. Yasich
Attorney, Agent, or Firm—Holman & Stern

[57] ABSTRACT

An indicator principally for measuring fat depth on animal carcasses includes a base and has a probe extending outwardly from the base. The probe defines at or adjacent its end remote from the base a first reference point and a moveable contact plate provides a second reference point. An indicator is provided to give an indication of the distance between the first and second reference points. An elastic means is provided between the base and the contact plate, the elasticity of the elastic means, which in the preferred form comprises springs, being selected so that in use the contact plate compresses the material, such as the surface of the animal carcass, by a predetermined amount.

7 Claims, 2 Drawing Figures

ANIMAL FAT INDICATOR

This invention relates to indicators and has been devised particularly though not solely as an indicator for measuring fat depth on an animal carcass.

When measuring fat depth on an animal carcass there can be a difficulty in that the fat depth can vary between hot and cold carcasses, that is to say between carcasses at or shortly after killing and the carcass when cold, or more often chilled. If it is desired to know the chilled fat depth this can be difficult or at least inconvenient to achieve because the most appropriate and simple time to measure the fat depth is shortly after killing. In particular if the fat depth is read at killing such reading need not be effected in undesirable working conditions such as the interior of the chiller or freezer.

It is therefore an object of the present invention to provide an indicator which will go at least some distance towards providing an indicator which will allow cold fat depth to be measured on a hot carcass or which will at least provide the public with a useful choice.

Accordingly the invention consists in an indicator comprising a base a probe extending from said base and insertable into an animalcarcass, said probe defining at or adjacent its end remote from said base a first reference point, a contact plate providing thereon a second reference point, display means provided to give an indication of the distance between said first and second reference points, and elastic means between said base and said contact plate, the elasticity of said elastic means being selected so that in use said contact plate compresses material, the depth of which is to be determined by an amount substantially equal to the expected shrinkage of the fat layer of the carcass.

To those skilled in the art to which this invention relates, many changes in construction and widely differing embodiments and applications of the invention will suggest themselves without departing from the scope of the invention as defined in the appended claims. The disclosure and the description herein are purely illustrative and are not intended to be in any sense limiting.

Figure 2:
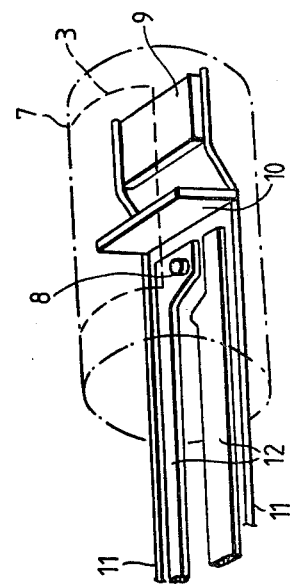

One preferred form of the invention will now be described with reference to the accompanying drawings in which:

FIG. 1 is a diagrammatic cross-sectional view of part of an indicator according to the invention, and FIG. 2 is a diagrammatic perspective presentation of part of a lance as used in the embodiment of the invention shown in FIG. 1.

In the invention an indicator is provided particularly for use in measuring the fat depth on an animal carcass and the indicator comprises a base 1 which, in the preferred form, forms a part of a housing 2. A lance 3 extends from the base 1 and in the preferred form of the invention the lance 3 is fixed to a support 4 within the housing 2 and extends outwardly through an aperture 5 in the base 1. The support 4 may be a cross piece between the walls of the housing 2 or may comprise the rear wall of the housing. A bearing 6 is preferably provided in aperture 5, preferably to provide a substantially liquid proof seal between housing 2 and bearing 6. The lance 3 includes a first reference point which may take the form of a light source 8 and light sensitive element 9 positioned closely together, for example, at 7 so that the light sensitive element may determine whether there is any reflected light or may determine variations in light intensity or colour as seen by the light sensitive element. Any such changes will, of course, depend upon the colour of the light emitted from the light source and the colour of the environment in which the light source is positioned. The first reference point is therefore at the position of the light sensitive element 9. The light source 8 preferably comprises a source of monochromatic light and is desirably green in colour such as a gallium phosphide green light emitting diode packaged in a green clear lens. The light sensitive element 9 is preferably a photo cell 9 such as a geen sensitive silicon cell. Green is a preferred colour as it is substantially opposite to the colour red of the spectrum. An optical barrier 10 is provided between light source 8 and photo cell 9 and electrical connections 11 and 12 are provided within lance 3. A contact plate 13 is provided, the front face 14 of which comprises a second reference point and elastic means 17 are provided between the base 1 and the contact plate 13. In the preferred form the contact plate 13 comprises an apertured plate positioned about the lance 3 mounting a tubular part 14 which extends into the interior of the housing 2 and terminates in a connection with a back plate 16. The extension 15 passes through bearing 6 preferably in a liquid proof manner. Between the back plate 16 and the rear of the wall or base 1 are provided the elastic means which, in the preferred form, take the form of a pair of springs 17, although more springs may be provided or, alternatively a single spring. Means to enable the distance between the reference points to be measured are provided and these may comprise a light emitter 18 and photo cell 19 with a finely divided grille 20 provided there between. (The figure is diagrammatic only, the light emitter 18 and photo cell 19 being shown on the same side of grille 20). Thus, as the contact plate 13 moves the grille or grid 20 will pass between the photo cell 19 and light source 18 causing changes in the output from the photo cell 19 which can be read on a suitable reading mechanism. Other indicating devices are possible.

The elasticity of the elastic means, for example, and in particular, the springs 17 is such that when the lance 3 is inserted, for example, into the fat layer 21 of an animal carcass the face 14 of the contact plate 13 will bear against the outer surface 22 of the fat layer 21 in a manner such that the springs 17 will cause some resistance to movement of the contact plate 13. This will cause the contact plate 13 to compress the fat layer 21 to at least some extent. By suitable selection of the elasticity of the springs 17 this compression is able to be made substantially equal to the shrinkage that will occur between hot and cold conditions of the fat, that is to say, between freshly killed and chilled meat. The construction is such that as the light source at 8 passes from the fat layer 21 into a meat layer 23 a change in light sensed by the photo-electric cell 9 at the reference point 7 will change. Means are provided to allow an indication of this also to occur so that a reading from the scale 20 can be taken at that stage although it is envisaged that these functions could be combined in a suitable reading apparatus.

It is also envisaged that the elasticity of the springs 17, will at least initially, be determined by empirical methods, that is to say, by trial and error, although the elasticity could in some circumstances be calculated. In general however a carcass is selected and measurements made of the carcass in the hot and cold states by indicators having springs of differing elasticity until a reading is obtained for the hot carcass that is correct for the cold carcass. This then sets the spring elasticity for carcasses of that type and age. The area of the contact plate may also be varied to change the compression of fat layer obtained. A larger contact plate gives less depth of compression.

The lance 3 is inserted into the fat of an animal carcass and the contact plate 13 is compressed against the surface 22 of the fat layer 21, the springs 17 being extended as the contact plate 13 moves into the housing. The elasticity of the springs will cause some resistance to movement of the contact plate 13 and this resistance to movement will cause pressure on the fat layer 21 by the contact plate 13 thus causing some depression of the fat layer 21 which depression is substnatially equal to the shrinkage that will occur between the hot and cold conditions of the fat layer. The indicating means will provide an indication of the fat depth at which the fat forms an interface with the meat layer.

Thus it can be seen that an indicator is provided which at least in the preferred form will provide an indication of the depth of fat on a carcass and it is a particular advantage of the preferred form of the invention that the fat depth may be read when the fat is in a hot or freshly killed condition so as to provide an indication of the fat depth when the carcass is in a cold or chilled condition. It is also an advantage of the invention that the mechanism to provide this is of a relatively simple nature. It is also believed that by suitable selection of the elastic means, the fat depth indicator can be used when the carcass is in the hot fat condition to provide a reading which will be accurate to within 2 mm or less when the fat is in the cold fat conditions.

What is claimed is:

1. An indicator for measureing the fat layer depth of an animal carcass comprising a base, a probe, means fixedly securing said probe with respect to said base, said probe extending from said base and insertable into an animal carcass, a first reference point defined as part of said probe and disposed proximate the probe and remote from said base, a contact member having defined thereon a second reference point, display means for providing an indication of the distance between said first and second reference points, and elastic means connected between said base and said contact member for elastically opposing increased separation of said first and second reference points, said contact member being positioned to contact said animal carcass upon insertion of said probe into said carcass to a predetermined depth, the elasticity of said elastic means being selected so that in use said contact member, upon contacting the carcass, compresses the carcass fat layer to a depth which is substantially equal to the expected shrinkage of the carcass fat layer before said probe can be further inserted into the carcass.

2. An indicator as claimed in claim 1 wherein said shrinkage comprises the shrinkage of said fat layer between hot and cold conditions of said carcass.

3. An indicator as claimed in claim 1 wherein said base comprises a housing and said probe extends from said housing, said contact member including an apertured plate positioned about said probe.

4. An indicator as claimed in claim 3 wherein parts of said contact member extend into said housing through an aperture in said housing and said elastic means are provided between said parts of said contact plate within said housing and the inner wall of said housing.

5. An indicator as claimed in claim 3 wherein said elatic means comprise one or more springs connected between said contact member and said housing.

6. An indicator as claimed in claim 3 wherein said contact member includes a back plate within said housing, said spring or springs being provided between said back plate and said housing so as to extend as said contact member is moved towards said housing.

7. An indicator as claimed in claim 3 further including display means which display means include a light emitter and a photo cell within said housing and a grille or grid positioned between said light emitter and said photo cell said grille or grid being mounted on said contact member to be moved as said contact plate is moved.

* * * * *